United States Patent [19]

Mercer

[11] Patent Number: 4,871,759
[45] Date of Patent: Oct. 3, 1989

[54] METHOD OF TREATMENT OF MESENTERIC ADENITIS

[76] Inventor: James B. Mercer, 13109 W. 95th St., Lenexa, Kans. 66215

[21] Appl. No.: 720,021

[22] Filed: Apr. 4, 1985

Related U.S. Application Data

[63] Continuation-in-part of Ser. No. 407,808, Aug. 13, 1982, Pat. No. 4,537,775, which is a continuation-in-part of Ser. No. 64,072, Aug. 6, 1979, Pat. No. 4,346,095, which is a continuation-in-part of Ser. No. 876,618, Feb. 10, 1978, Pat. No. 4,177,281, which is a continuation-in-part of Ser. No. 656,336, Feb. 9, 1976, Pat. No. 4,073,988, which is a continuation-in-part of Ser. No. 514,798, Oct. 15, 1974, Pat. No. 3,952,103, which is a continuation-in-part of Ser. No. 370,952, Jun. 18, 1973, Pat. No. 3,856,966.

[51] Int. Cl.$^4$ .................................. A61K 31/415
[52] U.S. Cl. .................................. 514/398; 514/400
[58] Field of Search .................................. 514/398, 400

[56] References Cited

PUBLICATIONS

Hollingshed Peritoneal Cavity and Mesenteries, Textbook of Anatomy, 2nd Ed, pp. 115–116, 1967.
Ursing et al., Metronidazole for Chron's Disease, The Lancet, pp. 775–777, Apr. 5, 1975.
Paul Urtrasun, M.D. et al., Radiation and High Dose Metronidazole in Supratentoreal Glioblastomas, New England Journal of Medicine, vol. 294, No. 25, pp. 1364–1367, Jun. 17, 1976.
Kenneth G. Warren, M.D. et al., Isolation of Latent Herpes Simplex Virus From the Superior Cervical and Vagus Ganglions of Human Beings, New England Journal of Medicine, vol. 298, No. 19, pp. 1068–1069, May 11, 1978.
Van Der Spey, et al, Cimetidiene in the Treatment of Herpesverus Infections, S. A. Mediesi Tydskrif, pp. 112–116 Jul. 19, 1980.
Bernstein, et al, Healing of Perineal Chron's Disease with Metronidazole, Gastrosenterology, 79:357–365, 1980.
Brandt et al, Metronidazole Therapy for Perineal Chron's Disease; A Follow–Up Study, Gastroenterology, 83:383–387, 1982.
Hayne and Mercer; Herpes Zoster: Treatment with Cimetidine, The Canadian Medical Assoc. Journal, vol. 129, Dec. 15, 1983.
Geigler, et al, Interaction Between Cimetidine and Metronidazole, Journal of Medicine, vol. 309, No. 24, pp. 1518–1519, Dec. 15, 1983.
Maulight et al., Cimetidine for Herpes Zoster, Journal of Medicine, vol. 310, No. 5, pp. 318–319, Feb. 2, 1984.
News Front, Zinc: Speeding Recovery From the Common Cold, Modern Medicine, Jul., 1984.

Primary Examiner—Jerome D. Goldberg
Attorney, Agent, or Firm—Litman, McMahon & Brown

[57] ABSTRACT

A method of treatment for mesenteric adenitis in humans is provided. The method comprises the administration of antiviral agents comprising pharmaceutical derivatives of imidazole. Specifically, mesenteric adenitis is treated with orally administered dosages of metronidazole or cimetidene. When the treatment is with metronidazole, a preferred dosage for average sized adult humans is approximately 1,000 to 2,000 milligrams administered once a day. When the antiviral agent administered is cimetidine, the preferred dosage is 900 to 1,200 milligrams given two times a day. When either cimetidine or metronidazole are given, concurrent treatment with zinc is suggested as a method of speeding recovery.

4 Claims, No Drawings

METHOD OF TREATMENT OF MESENTERIC ADENITIS

CROSS-REFERENCE TO RELATED APPLICATIONS

This is a Continuation-in-Part of application Ser. No. 407,808 filed Aug. 13, 1982, entitled THERAPEUTIC TREATMENT FOR VIRAL INFECTIONS, now Pat. No. 4,537,775, which was a Continuation-in-Part of 064,072, filed Aug. 6, 1979, now Pat. No. 4,346,095; which was a Continuation-in-Part of Ser. No. 876,618, filed Feb. 10, 1978, now Pat. No. 4,177,281; which was a Continuation-in-Part of Ser. No. 656,336, filed Feb. 9, 1976, now Pat. No. 4,073,988; which was a Continuation-in-Part of Ser. No. 514,798, filed Oct. 15, 1974, now Pat. No. 3,952,103; which was a Continuation-in-Part of Ser. No. 370,952, filed June 18, 1973, now Pat. No. 3,856,966.

BACKGROUND OF THE INVENTION

The invention herein described relates to a method of treating mesenteric adenitis in humans. Although applicant does not intend to be held to a particular theory, applicant believes that the treatment is effective as the result of control of viral causes of the condition.

The mesentery is a peritoneal fold, encircling the greater part of the small intestine and connecting the intestine to the abdominal wall. Occasionally, the mesenteric lymph nodes can become inflamed, a condition known as mesenteric adenitis. The causes of mesenteric adenitis are not fully understood; however it appears that viral illnesses can cause the mesenteric lymph nodes to become swollen and reactive. This condition can cause patients considerable abdominal discomfort.

OBJECTS OF THE INVENTION

The objects of this invention are: to provide a method for systematically treating virally induced mesenteric adenitis in humans; to provide such a method which comprises treatment with antiviral agents having an imidazole moiety therein; to provide such a method of treatment which comprises the administration of 1-(beta-hydroxy)-2-methyl-5-nitro-imidazole (metronidazole); to provide such a method which comprises administration of $N^{11}$-cyano-N-methyl-$N^1$-[2[[(5-methyl-1H-imidazol-4-yl)methyl]thio]-ethyl]guanidine (cimetidine); to provide such a method which includes concurrent treatment with a source of zinc, to speed recovery; and to provide such a method of treatment which is relatively easy to effect.

Other objects and advantages of this invention will become apparent from the following description taken in connection with the presented case studies, wherein are set forth certain applications of the present invention.

SUMMARY OF THE INVENTION

Metronidazole is a known alkylating agent, of relatively low toxicity in mammals, which is thought to interfere with nucleic acid biosynthesis. It appears to applicant that metronidazole can penetrate all tissues of the body quite readily and its effectiveness, in the treatment of viral infections, is believed by applicant to relate to blockage or interference with the viral metabolism cycle necessary for cell infection. The agent apparently supresses viral production while natural body defenses function to eliminate viral material from the system. Metronidazole is readily absorbable from the human intestinal tract and may be administered orally, as well as intraveneously, or by vaginal or rectal inserts, as indicated.

Metronidazole is believed by applicant to be effective in treating many viral conditions in humans, such as regional ileitis (Crohn's disease), viral thyroiditis, multiple sclerosis, viral hepatitis, carpal tunnel syndrome, psoriasis, amyotrophic lateral sclerosis, cytomegalovirus infection, viral bilateral macular degeneration of the retina, sarcoidosis, viral diverticulitis, measles (Rubeola), herpes simplex viral, herpes zoster viral, infectious mononucleosis, atheroarteriosclerosis, rheumatoid arthritis and juvenile rheumatoid arthritis. Treatment of humans with metronidazole may be effective in the extension of the life span, resulting from an inhibition of continuing viral diseases. In other mammals, viral diseases, such as distemper, apparently respond to the treatment. Applicant believes that mesenteric adenitis is aggravated by some of the same viruses which cause the above disorders and that it may be treated by anti-viral agents.

A typical intense treatment, with metronidazole, for an average sized human adult patient comprises 1000 to 2000 milligrams (mgs) of the agent given in a single, daily oral bolus dose, with a dosage reduction as the condition improves. Doses for children and veterinary use are proportionally less according to body weight. An alternative is to give 500 mg. three times per day. The first method of higher dosage levels given once per day may help protect the patient from developing a peripheral neuoropathy. The larger the dose, the longer should be the time between doses, for example, five to ten grams of metronidazole may be given three times per week, generally with safety from peripheral neuropathy. An effective long-term maintenance dose may be as low as 31 mgs. per day.

Regarding side effects, some persons may experience nausea. In rare instances, there may be a slight soreness of the mouth, or a white tongue, indicating need for dosage reduction. Some dizziness and dryness of the mouth and vagina are occasionally noted and some patients complain of a bad taste.

Metronidazole is believed contraindicated in patients under treatment with desulfadram (Antabuse) and in hypothyroid patients. Because metronidazole appears to cross the placental barrier and enter the fetal circulation rapidly, and since its effects on fetal development are generally known, it should be given during the first trimester of pregnancy if a viral infection is suspected. Metronidazole, when given in the first trimester of pregnancy, may reduce the chances of still births, and both major and minor fetal abnormalities. It appears that metronidazole should be given at any time during pregnancy that the mother has a viral disease, so as to prevent mental retardation and other fetal abnormalities.

The initial neurological signs of metronidazole overdose in humans appear to be increased pulse rate, difficulty in reading small print, difficulty in handling small objects and insomnia. Progressively, it is understood that tachycardia may occur, and a slightly unstable person, especially, may suffer marked swings in mood. Physical exercise apparently becomes increasingly fatiguing, and weight loss occurs in spite of substantial food intake. When the medication is withdrawn, the adverse reaction usually clears in one week.

The metronidazole treatment described does not appear to damage the hematopoietic or the reticuloendothelial systems.

Over the past several years, metronidazole has been tried with varied effectiveness for the treatment of trichomonas vaginalis infections, alcoholism, ameobic dysentary, amoebic liver abcess, leishmaniasis and giardia infestations, acute ulcerative gingivitis, long standing indolent ischemic ulcers found in peripheral vascular disease, scleroderma, schizophrenia and in diabetic retinopathy, but apparently its general effectiveness against viral infections has not been widely known.

Metronidazole apparently interferes directly with the synthesis of DNA viruses, in a similar manner that occurs with cytosine arabinoside. Metronidazole also apparently interferes with protein synthesis, as uric acid levels increase during therapy, and may in some instances manifest itself in acute gout.

Metronidazole is found to be an anti-viral agent that does not damage the mammalian immune system and is known to be active against DNA and RNA viral infections. These viral diseases, when uncontrolled for long periods of time, may cause death from the degenerative diseases of aging that lead to key organ failure.

It appears that viral diseases often form reservoirs of infection in the neural ganglions of the central and spinal nervous system; and, from these sites or reservoirs, they bombard key target organs by movement over neural pathways until death occurs from malignant transformation of the chromosomes in the affected target or key organ cells or until viral arteritis leads to key organ death by obstruction of the arterial blood flow. It appears to applicant that metronidazole is capable of controlling the latent viral disease if given in sufficient dosage over a period of time.

Applicant believes that a critical chemical feature of metronidazole, in its success as an antiviral agent, is that it is a derivative of imidazole. Imidazole is 1,3-diaza-2,4-cyclopentadiene. It was foreseen by applicant that the closely related compound, cimetidine, also a derivative of imidazole, would show analagous activity against mesenteric adenitis, as well as mixtures of metronidazole and cemetidine. This expectation was born out in clinical use, as reported below in specific case studies. Applicant believes that numerous pharmaceutical derivatives of imidazole, if sufficiently non-toxic and possessing appropriate bioavailability to be transported to a site of viral infection, will be effective against mesenteric adenitis.

A zinc source, such as zinc sulfate may be used concurrently with cimetidine or metronidazole, in treating virally caused mesenteric adenitis. Any pharmaceutically acceptable source of zinc may be utilized. Applicant believes that any non-toxic increase in zinc levels will be effective in aiding recovery; however, a zinc sulfate dose of 200 mg. taken three times a day, preferably with food, for an average sized adult concurrently undergoing treatment with an imidazole-derivative anti-viral agent, such as metronidazole or cimetidine, is preferred.

The following cases are presented to show examples of methods according to the present invention and are not meant to be limiting.

CASE STUDY 1

The patient was a 21 year old caucasian male. The patient had a history of having marked right lower quadrant abdominal pain. The patient was seen and reported excessive abdominal pain and pain on walking. He had an oral temperature of 100.6° Fahrenheit and reported having been ill for several days with associated nausea and vomiting. His white blood count was somewhat elevated. He had been seen at a local hospital emergency room where a diagnosis of probable mesenteric adenitis had been made.

Shortly after the visit to the local hospital emergency room, the patient was seen by the applicant. He appeared to have an ileus, had point and rebound tenderness and a marked decrease in bowel sounds. The patient was started on metronidazole, 250 mgs. administered three times per day (t.i.d.). After 24 hours, the patient's lower abdominal discomfort had decreased, his nausea had decreased and his temperature was somewhat lower than the prior day. The patient had infrequent bowel sounds of fair quality and his point and rebound tenderness had decreased. The patient was now able to tolerate oral soda pop in small amounts. After 48 hours of treatment, the patient still had minimal right lower quadrant tenderness and was passing gas rectally. However, no rebound tenderness was present and the patient was tolerating oral liquids well. After 72 hours of treatment, the patient was tolerating soft food and was starting to have bowel movements. His abdomen was no longer tender and he was afebrile. The patient continued on metronidazole therapy for several more days, at which time the drug was discontinued with full recovery.

It appeared that this patient had a viral induced illness that caused the mesenteric lymph nodes to become swollen and reactive. Applicant believes that the antiviral agent metronidazole controlled the viral illness and substantially shortened the usual course of the mesenteric adenitis.

CASE REPORT 2

This patient was a 38 year old caucasian female. The patient was seen with a severe sore throat and a circular patch of herpes vesicles on her chin. The vesicles measured approximately 0.75 inches in diameter. The patient's lymph nodes were markedly swollen above the trachea and she had difficulty in swallowing. The patient had recently been a participant in a group exercise that required going without rest or sleep for approximately 48 hours. It was shortly after that time that she noted the onset of herpes simplex virus, reflected by the appearance of the vesicles. She was asked if she had ever had a similar experience in the past. She reported that two years prior, under similar circumstances, she had noted the vesicles on her chin appearing when she had been unable to get her usual nightly sleep. The patient was given a pain killer including acetaminophen for pain. Specifically, she was given a pain killer sold under the trade name Tylenol No. 3, in an amount of one or two tablets every four hours, or as necessary.

The patient was seen again 48 hours later. At this time, the patient had a marked lower abdominal distension, her bowel sounds were minimal with an occasional bubbling sound of poor quality being heard. Palpation of the abdomen elicted point and rebound tenderness. The vesicles had remained the same in appearance with no further eruption. Palpation of the involved cervial chain of lymph nodes on each side of the throat generated less pain and it was not painful for her to swallow. The patient reported that as her abdomen became more distended she tended to become nauseated and she was unable to pass sufficient gas rectally to reduce her pain.

A complete blood count was done and it was not elevated, however, there was an increase in the number of lymphocytes with the right shift. The patient was instructed to return in 24 hours for reevaluation.

When the patient was seen again, she reported increased lower abdominal discomfort, with pain on walking. The patient was now becoming increasingly nauseated. She was having difficulty sipping even a small amount of soda pop and she was not passing as much gas rectally as before. An occasional tinkling bowel sound was heard, which was of poor quality. It was felt, at this time, that her apparent herpes simplex virus one had entered the long vagal tract in the area of her cervical nodes. The viral infection may have been causing an inflammatory reaction in the mesenteric lymph nodes, causing her ileus. Her abdomen was quite tympanic and palpation caused marked abdominal pain. The patient was started on cimetidine, 900 mgs. taken two times daily (b.i.d.). After 48 hours of cimetidine therapy, the vesicles on her chin were drying, she had lost her abdominal distension and was passing gas easily. At this point, she was no longer nauseated and her abdominal pain was essentially gone. The patient was treated for a week on this regimen at which time the cimetidine was discontinued.

It appears that this patient had a border-line immunity to herpes simplex virus one that becomes activated when she is not able to sleep every night to regain her strength. Applicant believes that the herpes simplex virus type one may have induced the mesenteric adenitis.

It is foreseen that the above two examples represent specific instances of a general treatment methodology for mesenteric adenitis. Generally, the mesenteric adenitis will have been caused by a viral infection. Treatment with an antiviral agent including the imidazole moiety will be generally effective in relieving the condition. Generally, the agent should be relatively nontoxic, in pharmaceutically effective amounts. Also, it needs to have sufficient bioavailability to be readily transported to a site of viral infection. Specifically, metronidazole or cimetidine should be prescribed.

Generally, metronidazole is readily tolerated in amounts of approximately 250 mg three times a day; however, intense treatment comprising 500 mg of the agent three to four times a day can usually be tolerated. Doses for children are usually proportionally less according to body weight.

Generally, cimetidine can be tolerated in amounts of up to approximatley 2,400 mg per day. The dosage of 900 mg b.i.d. until relief, is, at this time, believed by applicant to be the preferred dosage. The dosage for children would be proportionately lower, depending upon body weight.

It is to be understood that while certain forms of the present invention have been described, it is not to be limited to the specific methods described herein.

What is claimed and desired to be secured by Letters Patent is as follows:

1. A method for treating a human host having virally induced mesenteric adenitis; the method comprising:
    (a) repeatedly orally administering a pharmaceutically acceptable amount of an anti-mesenteric adenitis effective antiviral agent comprising metronidazole and possessing sufficient bioavailabilty to be transported to a situs of viral infection.
2. The method of claim 1 wherein:
    (a) an additional antiviral agent, cimetidine, is added in an effective amount.
3. The method of claim 1 including:
    (a) adminstering the metronidazole in dosages of about 250 mg. three times a day, until the mesenteric adenitis is relieved.
4. The method of claim 1 including:
    (a) administering the metronidazole in a single dose of between 1,000 and 2,000 mg., once a day, until the mesenteric adenitis is relieved.

* * * * *